United States Patent
Gallardo

(10) Patent No.: US 9,733,204 B2
(45) Date of Patent: Aug. 15, 2017

(54) WORKING ELECTRODE PRINTED ON A SUBSTRATE

(75) Inventor: Manuel Antonio Raymond Gallardo, Thorigny-sur-Marne (FR)

(73) Assignee: Easy Life Science, Paris (FR)

( * ) Notice: Subject to any disclaimer, the term of this patent is extended or adjusted under 35 U.S.C. 154(b) by 691 days.

(21) Appl. No.: 14/236,834

(22) PCT Filed: Aug. 3, 2012

(86) PCT No.: PCT/EP2012/065293
§ 371 (c)(1),
(2), (4) Date: Apr. 10, 2014

(87) PCT Pub. No.: WO2013/017697
PCT Pub. Date: Feb. 7, 2013

(65) Prior Publication Data
US 2014/0224652 A1     Aug. 14, 2014

(30) Foreign Application Priority Data

Aug. 4, 2011 (FR) ...................... 11 02444

(51) Int. Cl.
*G01N 27/30* (2006.01)
(52) U.S. Cl.
CPC .................. *G01N 27/308* (2013.01)
(58) Field of Classification Search
CPC ................................................ G01N 27/308
See application file for complete search history.

(56) References Cited

U.S. PATENT DOCUMENTS

| | | | |
|---|---|---|---|
| 5,672,257 A | 9/1997 | Birch et al. | |
| 6,423,193 B1 | 7/2002 | Miller et al. | |

(Continued)

FOREIGN PATENT DOCUMENTS

| | | |
|---|---|---|
| FR | 2 898 133 A1 | 9/2007 |
| JP | H09-166571 A | 6/1997 |
| RU | 94713 U1 | 5/2010 |

OTHER PUBLICATIONS

Office Action in corresponding Japanese Patent Application No. 2014-523343 mailed Jun. 24, 2014 (3 pages).
(Continued)

*Primary Examiner* — Jill Warden
*Assistant Examiner* — Julie Tavares
(74) *Attorney, Agent, or Firm* — Osha Liang LLP

(57) ABSTRACT

Device comprising a substrate (1), an electrode (2), a track (4) and a recess (3), wherein the substrate extends over a first thickness, between a first face and a second face, wherein the electrode is printed on the first face, wherein the track is printed on the second face, wherein the substrate is electrically insulated, wherein the electrode is conductive to electricity essentially through carbon particles, wherein the track is conductive to electricity and contains particles of silver, wherein the recess is conductive to electricity and is made of an ink which comprises a binary mixture of carbon and silver in proportions where the quantity of silver divided by the sum of the quantities of carbon and silver present in the binary mixture is comprised within a 0 to 1 interval, wherein the recess extends within the substrate from the first face to the second face, wherein the recess is in electrical contact with the electrode at the level of a first junction located on the first face, wherein the recess is in electrical contact with the track at the level of a second junction located on the second face, and wherein the linear density of silver particles in the recess at the level of the first junction, perpendicularly to the current lines when a current passes through the first junction, is lower than the linear density of silver particles in the track at the level of the second junction, perpendicularly to the current lines when a current passes through the second junction. By using such binary mixture of carbon and silver in the recess (3), silver contamination in electrochemical cells using silver tracks is reduced.

10 Claims, 1 Drawing Sheet

(56) References Cited

U.S. PATENT DOCUMENTS

Figure 1:
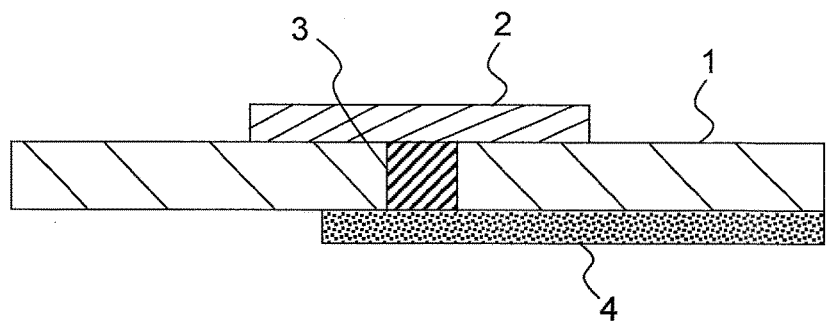

2004/0149578 A1     8/2004   Huang
2004/0256228 A1   12/2004   Huang
2006/0011474 A1     1/2006   Schulein et al.

OTHER PUBLICATIONS

Office Action in corresponding European Patent Application No. 12750555.0 dated Nov. 14, 2014 (4 pages).
International Search Report issued in PCT/EP2012/065293 mailed on Oct. 5, 2012 (3 pages).
Written Opinion of the International Searching Authority issued in PCT/EP2012/065293 mailed on Oct. 5, 2012 (7 pages).
Decision on Grant issued in corresponding Russian Patent Application No. 2014108037/28(012779), mailed on Nov. 29, 2016 (15 pages).

WORKING ELECTRODE PRINTED ON A SUBSTRATE

The present disclosure relates to the field of electrochemical cells printed on a substrate and particularly to the manufacture of a working electrode for such a cell through printing techniques, using inks made of mixtures of particles of polymer, carbon and silver, for the purpose of analyzing electrolytic solutions.

An electrochemical cell printed on a substrate usually comprises three electrodes, a working electrode, a reference electrode and a counter electrode. Each of these electrodes is connected by a conductive track to an electric circuit operable automatically which essentially allows a difference in potential between the working electrode and the reference electrode to be imposed and a current in an electric circuit comprising the working electrode and the counter electrode in series to be measured.

Printed electrochemical cells are usually produced on a substrate that is essentially planar and thin, with a typical thickness of 80 microns to 120 microns, such as a polyester sheet and comprising a first face on which the electrodes are printed and a second free face. The printed cells are produced in numbers in the form of a matrix which allows for several measurements of the same electrolyte or different electrolytes in parallel, particularly in the field of health.

In order to attain the electrochemical measurements of an electrolyte, the substrate is placed flat, its second free face facing downwards and its first printed face facing upwards, and a cover pierced with holes is affixed to the first face by gluing or welding, sealed with respect to the intended electrolyte, the base of the holes being aligned to the substrate, so that the electrodes of the cells, necessary for the electrochemical measurements, overlay the base of the well. The wells are then filled with an electrolytic solution, typically liquid. The electrochemical cells are finally powered in sequence by a single electrical circuit fitted with a multiplexer that allows each cell to be measured independently.

Inks are of considerable importance in the development of a printed electrochemical cell and the availability of inks allowing the manufacture of a complete cell is essential. Inks made of a polymer charged with a binary mixture of particles of carbon or silver in solution in a volatile solvent are commonly used in this field. The solvent evaporates once the ink is printed on a surface, i.e. a thin layer of deposit on this surface, a percolation appears between the particles in solution in the polymer and an electrical conduction is observed based on the concentration of particles of carbon and silver.

When the binary mixture is entirely or almost entirely chemically inert in a wide range of electrochemical potentials, i.e. essentially made of carbon particles, the ink is ideal for manufacturing working electrodes of good quality. Indeed the presence of silver, chemically active, in a working electrode, on its contact surface with the electrolyte, significantly degrades its performance by the activation of oxydoreduction reactions that disrupt the signal of the measurement and decrease stability, thereby reducing accuracy and usefulness.

When the binary mixture is essentially made of silver particles, its electrical resistance is by comparison much lower than that of a mixture of particles of carbon of the same concentration, in equal volume. Such a binary mixture is particularly well suited for manufacturing conductive tracks to transport the electrical current from the surface of a working electrode and contact blocks passing through a substrate allowing to connect conductive tracks from both sides of the substrate.

A working electrode of carbon, the finest possible, connected to a track of silver thus provides, theoretically, the best structure for an electrochemical cell, depending on the type of ink of binary mixture of carbon and silver, by minimizing the resistance encountered by the electrochemical current in the electrical measuring circuit of the cell.

However, in practice, when the working electrodes are printed on a substrate with inks, this structure encounters a problem involving pollution of the surface of the working electrode by particles of silver from the track. Indeed, the presence of solvent during the deposit by printing causes an exchange of silver particles at the junction of a carbon electrode and a track by producing a gradation in silver concentration. Likewise, the polymers of the inks are affected by creeping causing migration of silver particles to the surface of a working electrode. In addition, the printed carbon electrodes may be porous; they may put the electrolyte in direct contact with the silver track.

Surface elements in which the concentration of silver is lower than in a track and higher than in an electrode are therefore intercalated in the electrical circuit of working electrodes in order to reduce the phenomenon of electrode contamination by the silver particles from the track. A circuit of a working electrode on one face only or single-faced thus consists commonly in the prior art of a working electrode with an ink of carbon, a track with an ink of silver and a silver buffer or silver depleted recess or a recess made of an ink which is a binary mixture of carbon and silver in proportions where the quantity of silver divided by the sum of the quantities of carbon and silver present in the mixture, or concentration of silver in the binary mixture, varies from 0, typically for an electrode, to 1, typically for a track or a contact block for the passage of a silver track across a substrate.

In the prior art, silver depleted recesses, in which there is no concentration of silver and which are electrode tails of carbon, are thus used to repel the silver particles of the electrode. The electrode is then lengthened by an extension containing no silver, limiting signal disturbance, and of empirically determined length.

However, the applicant has found that the presence of a recess causes a clutter of the printed surface but more importantly requires a bonding of the top cover comprising the wells and the substrate on a non-smooth surface, the electrode tail typically exceeding about 10 microns to 15 microns for a printing, a screen-printing for example. This irregular bonding surface causes long-term loss of sealing of the well or during repeated temperature cycles which are harmful to the metrology of an electrochemical cell where the working electrode has a recess that is nevertheless essential.

It would therefore be desirable in the case of printed electrochemical cells to transfer the silver tracks and the recesses to the free face to leave only the electrodes on the printed face or first face by passing the non-metrological elements that are the track and the recess to the second face of the substrate. In this way, a working electrode printed using the 'double-faced' technique as opposed to the 'single-faced' technique in which all the elements of the cell (working electrode, recess and track) are printed on a same face of the substrate would be obtained. In the double-faced technique, contact blocks made of silver paste are used, i.e. an ink consisting essentially of silver particles, in order to transfer a silver track from one face to the other.

However, for a double-faced electrochemical cell to be printed, it is necessary at the same time to retain an electrode tail of carbon in the inner diameter of the well, of which the cell will constitute the base after the bonding to the top cover, in order to avoid making it span a bonding surface of the top cover and the substrate and retain its length to act as silver depleted recess.

The surface of the working electrode being at its maximum, in order to increase the electrochemical signal, the silver depleted recess therefore takes in this area a part of the useful surface of the electrode and becomes a problem for the metrology of a printed electrochemical cell by reducing the electrochemical signal.

Advantageously, the silver depleted recess would therefore be situated on the second face.

It is then known from the prior art that the transfer of a silver track poses no particular problem, a silver contact block spanning the substrate in electrical contact with a first track on the first face and a second track on the second face, easily achieving this non-metrological operation, the track essentially carrying a current.

It is also known from the prior art that a contact block must be as conductive as possible, silver is thus the material of choice with regard to issues of cost, especially in this field, or a material of comparable conductivity, i.e. metallic.

It is again known from the prior art to place a silver contact block directly under the electrode despite problems expected from contamination, in the absence of chemically inert metallic conductive contact blocks and of comparable cost to silver.

However, it is not known from the prior art to place a silver depleted recess in series with the working electrode in an electrical circuit to measure the current of this electrode in the base of the well formed by the surface of the substrate on its first face that serves as a base for a well after bonding of a top cover.

Indeed, it is not possible to place an element with a high concentration of silver without protection at the surface because it would pollute the measurement and the applicant has found that it is not possible to place a silver track under the carbon working electrode because a pollution of silver is observed in the measurement, the 15 micron thickness of the printed electrode do not permit to obtain an effective recess of silver. It is also not possible for the same reason to have a silver contact block under the electrode.

The silver depleted recess of a carbon working electrode printed on a substrate possessing two faces must therefore, in the prior art, be retained on the first face of the substrate and outside the well where it induces sealing problems that the applicant has highlighted.

The problem of silver contamination of a printed working electrode therefore imposes, in the prior art, the use of a silver depleted recess and silver contact blocks, on the same face of the substrate as the working electrode and outside the measurement wells.

In this context, is disclosed a device comprising a substrate, an electrode, a track and a recess, wherein the substrate extends over a first thickness between a first face and a second face, wherein the electrode is printed on the first face, wherein the track is printed on the second face, wherein the substrate is electrically insulated, wherein the electrode is conductive to electricity essentially through carbon particles, wherein the track is conductive to electricity and contains particles of silver, wherein the recess is conductive to electricity and is made of an ink which comprises a binary mixture of carbon and silver in proportions where the quantity of silver divided by the sum of the quantities of carbon and silver present in the binary mixture is comprised within a 0 to 1 interval, wherein the recess extends within the substrate from the first face to the second face, wherein the recess is in electrical contact with the electrode at the level of a first junction located on the first face, wherein the recess is in electrical contact with the track at the level of a second junction located on the second face, and wherein the linear density of silver particles in the recess at the level of the first junction, perpendicularly to the current lines when a current passes through the first junction, is lower than the linear density of silver particles in the track at the level of the second junction, perpendicularly to the current lines when a current passes through the second junction.

According to variants of the present disclosure:
  said recess is conductive to electricity essentially through
    carbon particles.
  the silver depleted recess has a concentration of silver
    particles essentially equal to the concentration of silver
    particles of the track and the section of the recess,
    parallel to the first face, at the level of the first junction,
    has an area lower than that of the section of the recess,
    parallel to the second face, at the level of the second
    junction.
  the recess extends, within the substrate, according to a
    rotation cylinder around a cylindrical axis perpendicular to the first face.
  the recess extends, within the substrate, according to a
    first truncated cone around a first axis perpendicular to
    the first face, the section of the first truncated cone,
    parallel to the first face, decreasing from the second
    face to the first face.
  the recess extends, within the substrate, according to a
    second truncated cone around a second axis perpendicular to the first face, the section of the second
    truncated cone, parallel to the first face, decreasing
    from the first face to the second face.
  the recess extends, within the substrate, according to a
    third truncated cone around a third axis perpendicular
    to the first face, the section of the third truncated cone,
    parallel to the first face, at the level of the first junction,
    having a surface lower than the surface of the second
    junction.
  the recess includes a part printed on said second face, up
    to the second junction.

The present disclosure also relates to a method of obtaining a device such as the one above, including the stages of drilling a hole through said substrate from said first face to said second face, filling the hole with said ink to form said recess, printing, on the first face, said electrode, in electrical contact with the recess, printing, on the second surface, said track, in electrical contact with the recess.

The present disclosure also relates to a use of a device such as above as a working electrode of an electrochemical cell.

Embodiments of the present disclosure are described with reference to figures numbered 1 to 4, in which:

FIG. 1 represents in section according to a vertical plane, a horizontal substrate printed according to the present disclosure with an electrode made of ink of carbon on one of its faces, a cylindrical contact block made of ink of carbon spanning the substrate and a track made of ink of silver printed on the other face, the contact block being in electrical contact with the electrode and the track.

Figure 2:
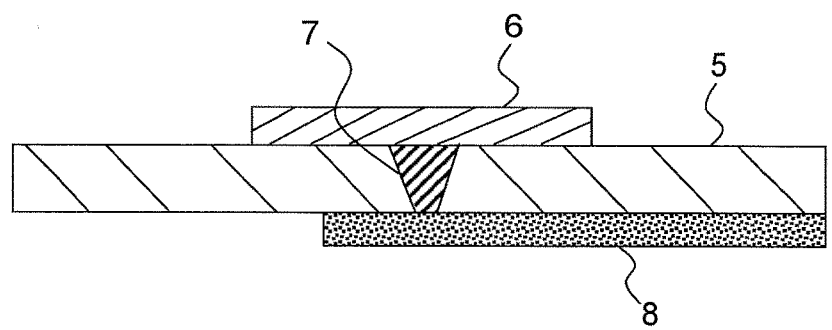

FIG. 2 represents in section according to a vertical plane, a horizontal substrate printed according to the present disclosure with an electrode made of ink of carbon on one of its faces, a truncated cone shaped contact block made of ink of carbon spanning the substrate and a track made of ink of silver printed on the other face, the contact block being in electrical contact with the electrode at its largest section or base and in electrical contact with the track at its smallest section or tip.

Figure 3:
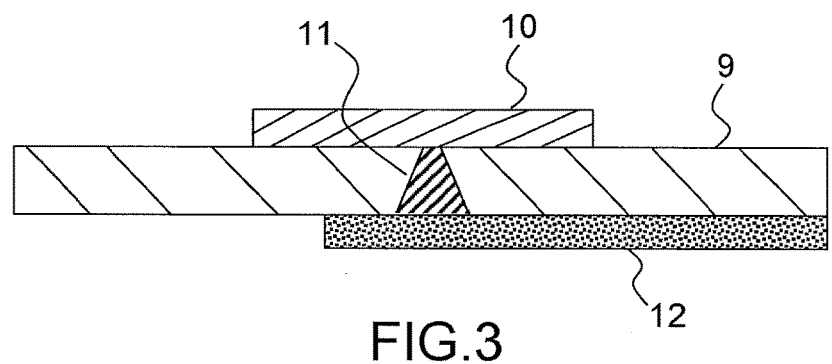

FIG. 3 represents in section according to a vertical plane, a horizontal substrate printed according to the present disclosure with an electrode made of ink of carbon on one of its faces, a truncated cone shaped contact block made of ink of carbon spanning the substrate and a track made of ink of silver printed on the other face, the contact block being in electrical contact with the electrode at its smallest section or tip and in electrical contact with the track at its largest section or base.

Figure 4:
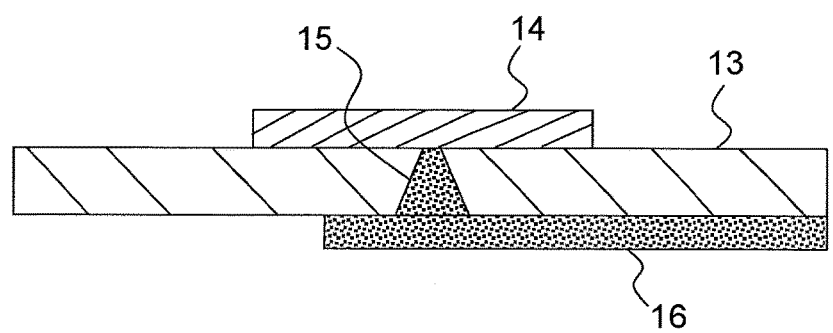

FIG. 4 represents in section according to a vertical plane, a horizontal substrate printed according to the present disclosure with an electrode made of ink of carbon on one of its faces, a truncated cone shaped contact block made of ink of silver spanning the substrate and a track made of ink of silver printed on the other face, the contact block being in electrical contact with the electrode at its smallest section or tip and in electrical contact with the track at its largest section or base.

According to a first embodiment with reference to FIG. 1, on a first substrate (1) made of 80 microns to 120 microns polyester, a first working electrode (2) made using a first ink of carbon is printed on a first face of the first substrate having a first essentially circular surface of 5 mm in diameter. This first electrode is printed in a first circle of 2 mm in diameter and is 10 to 15 microns in thickness. A first cylindrical hole spans the substrate and is covered by the first electrode, this hole is filled with the first ink to form a first cylindrical working contact block (3). Finally, a first track (4) is printed on a second face of the first substrate using a second conductive ink of silver. A part of this first track in contact with the first working contact block can be printed using said first ink of carbon to increase the distance from the recess of silver particles contained in the first track and from the first electrode. In this first method, printing with the first ink of the first electrode will be done, then the substrate will be returned and the first contact block printed with said first ink in the first hole. Finally, the first silver track will be printed on the second face of the first substrate.

According to a second embodiment with reference to FIG. 2, on a second substrate (5) made of 80 microns to 120 microns polyester, a second working electrode (6) which is a layer of ink of carbon or a layer of carbon within a second circle of 2 mm in diameter and 10 to 15 microns in thickness, is printed on a first face of the second substrate having a second essentially circular surface of 5 mm in diameter. A second truncated cone shaped hole spans the substrate and is covered by the second working electrode. This truncated cone shaped hole was filled by printing with said first ink of carbon to form a second truncated cone shaped working contact block (7), the second tip of which, typically a circular surface of 10 microns in diameter, comes in contact with the second face of the second substrate and the second base of which, typically a circular surface of 100 to 150 microns in diameter, comes in contact with the first face of the second substrate. Finally, a second track (8) is printed on a second face of the second substrate using said second ink of silver. A part of this second track in contact with the second working contact block can be printed using said first ink of carbon to increase the distance of the recess between silver particles contained in the second track and the second electrode. In this second method, embodiments of the present disclosure can be achieved in two printings rather than three for the first method. Indeed, it is possible to print the second electrode and the second hole with said first ink in a single step, from the first face of the second substrate, the tip of the second truncated cone shaped hole being small and preventing the releases of the first ink on the second face, then to print the second silver track in electrical contact with the tip of the second truncated cone shaped contact block. The composition of the first ink of carbon of the second contact block and the second bottleneck formed on the surface of the second track by the tip of the second cone, together provide an enhanced recess compared to said first method and an electrochemical signal of better quality compared to the first method, but also compared to a second contact block that would be cylindrical, having a base unchanged, being made of ink of silver, and which would not constitute a silver depleted recess.

According to a third embodiment with reference to FIG. 3, on a third substrate (9) made of 80 microns to 120 microns polyester, a third working electrode (10) which is a layer of ink of carbon or a layer of carbon within a third circle of 2 mm in diameter and 10 to 15 microns in thickness, is printed on a first face of the third substrate having a third essentially circular surface of 5 mm in diameter. A third truncated cone shaped hole spans the third substrate and is covered by the third working electrode. This third truncated cone shaped hole was filled by printing with said first ink of carbon to form a third truncated cone shaped working contact block (11), the third tip of which, typically a circular surface of 10 microns in diameter, comes in contact with the first face of the third substrate and the third base of which, typically a circular surface of 100 to 150 microns in diameter, comes in contact with the second face of the third substrate. Finally, a third track (12) is printed on the second face of the third substrate using said second ink of silver. A part of this third track in contact with the third working contact block can be printed using said first ink of carbon to increase the distance from the recess between silver particles contained in the third track and the third electrode. In this third method, embodiments of the present disclosure can be achieved in three printings. Indeed, it is possible to print the third electrode with said first ink on the first face of the third substrate, from the first face of the third substrate, the tip of the third truncated cone shaped hole being small and preventing the releases of the first ink into the third hole, then to return the third substrate and to print on the second face of the third substrate the third ink of carbon contact block, and finally, to print, on the second face of the third substrate, the third silver track in electrical contact with the base of the third truncated cone shaped contact block. The composition of the first ink of carbon of the third contact block and the third bottleneck formed on the first face of the third electrode, by the tip of the third cone, together provide an enhanced recess compared to said first method and an electrochemical signal of better quality compared to the first method, but also compared to a third contact block that would be cylindrical, having a base unchanged, and being made of ink of silver. This is the best method for achieving embodiments of the present disclosure.

According to a fourth embodiment with reference to FIG. 4, on a fourth substrate (13) made of 80 microns to 120 microns polyester, a fourth working electrode (14) which is a layer of ink of carbon or a layer of carbon within in a fourth circle of 2 mm in diameter and 10 to 15 microns in thickness, is printed on a first face of the fourth substrate having a fourth essentially circular surface of 5 mm in diameter. A fourth truncated cone shaped hole spans the fourth substrate and is covered by the fourth working electrode (14). This fourth truncated cone shaped hole was filled by printing with an ink of silver to form a fourth truncated cone shaped working contact block (15), the third tip of which, typically a fourth circular surface of 10 microns in diameter, comes in contact with the first face of the substrate in contact with the fourth electrode and the base of which, typically a fourth circular surface of 100 to 150 microns in diameter, comes in contact with the second face of the fourth substrate. Finally, a fourth track (16) is printed on the second face of the fourth substrate using said second conductive ink of silver in electrical contact with the fourth contact block. The effect of the recess of silver particles or recess of silver is obtained in this method only by the effect of the bottleneck obtained by the fourth surface of the tip of the fourth contact block, which is lower than the surface of the base of the fourth contact block in a manner that is further enhanced, which is lower than the section of the track that is perpendicular to the fourth substrate. In this fourth method, it is possible to manufacture the device of the present disclosure by a first printing on the first face of the fourth substrate of the fourth working electrode using a first ink charged with carbon particles, to return the fourth substrate and to print with said second ink of silver the fourth working contact block in electrical contact with the fourth electrode and the fourth track in electrical contact with the fourth contact block on the second surface. The printing can thus be performed in two operations. However, in this mode, the tip of the fourth truncated cone shaped contact block makes it possible to limit less effectively potential transmissions of silver particles between the fourth working contact block and the fourth working electrode, forming a bottleneck, if compared with respect to a fourth contact block which would become cylindrical and would remain with a base unchanged. This fourth method is a degraded method of the present disclosure but for which the effect of the recess exists effectively on the signal to noise ratio of a complete electrochemical cell using the device according to the present disclosure as a working electrode.

It will be understood in all cases that with regard to this application, without deviating from the information presented in the present disclosure, it is possible:

To exchange the polyester of the substrates for another material that can be printed on with inks that are binary mixtures of carbon and silver.

To exchange the screen printing technique for another printing technique compatible with inks that are binary mixtures of carbon and silver and in particular that make use of methods incorporating a pad or inkpad or injection or projection of ink.

To print without returning the substrate by using a printing method that is able to affect both its faces.

To insert, between the contact blocks made of said first ink and the tracks made of said second ink, an element of the track or an extension of the contact block made of said first ink and of variable length or doing the same for the contact blocks, introducing a bottleneck, these contact blocks being made of said second ink or an ink with less silver concentration than that of the track.

To use a second ink of silver which is a binary mixture of carbon and silver when the choice permits the use of the device of the present disclosure as a working electrode of a printed electrochemical cell comprising a counter electrode and a reference electrode or a complete electrochemical cell including a printed electrochemical cell, a well and an electrolyte.

To choose an inclination for holes and truncated cone shaped contact blocks, adapted to the silver concentration of the second ink, the tip surface decreasing for a contact block when the silver concentration of said second ink increases. To this end, the skilled person can make holes with varying inclination using various hole punches and examine the signal ratio of several complete electrochemical cells in parallel, using the same electrolyte but different sizes of hole or contact block tip, in order to determine the size adapted to an electrochemical application of the tip of a contact block or a hole having a truncated cone shape. Starting from a silver track of imposed size and equipped with a recess of given length when it is located on the first face of a substrate, a skilled person can test several dimensions of the tip of a hole or a contact block having a truncated cone shape, in order to obtain an improved signal to noise ratio when the substrate is printed on two faces.

To adapt the previous method to obtain from a third ink having an imposed concentration of silver, intermediate between the first and the second ink, a truncated cone shaped contact block having a tip tailored to the base of the truncated cone shaped contact block and to the section of the silver track in order to produce a silver depleted recess giving optimal quality of signal to noise ratio for the chosen inks.

To vary the diameters of the wells or the working electrodes.

To produce the holes using drill bits of varying diameter for the cylindrical holes or with punches of various types for the truncated cone shaped holes.

To produce truncated cone shaped sections, the generatrix of which, around an axis of revolution, is not equal to a straight line segment.

To reduce the linear density of silver particles of a silver track of an electrode, the linear density of particles in an electrical conductor being the product of the volume density of said particles by the section of the track perpendicularly to the current lines when a current passes through the conductor. The general method of the present disclosure may indeed be seen as a way to reduce, at the electrode, the linear density of silver particles brought to the electrode by a track or a contact block, i.e. a conductor containing silver. Indeed, when the contact block is made of silver, the recess is implanted at the level of the surface between the contact block and the electrode, the surface decreasing to reduce the linear density and when the contact block is made of carbon, the volume density of silver is nullified by embodiments of the present disclosure, to reduce the linear density between the track and the electrode.

It will be understood, in all the application, that when printing one element and then another, the two elements are in electrical contact upon completion of the printing, the printing being intended to produce an electrical circuit including an electrode, a contact block, also called 'via', and a track.

It will also be understood that the term 'silver depleted recess' may be understood as a mean to move away from a source of silver particles or to reduce the passage of silver particles by a conductor, in particular of the track or contact block type.

It will be also understood, in all the present application, that an ink made with a binary mixture of particles of silver and carbon may be either an ink comprising carbon, an ink comprising silver, or an ink comprising a non-null concentration of silver and a non-null concentration of carbon. For the purpose of the present application, an ink conductive to electricity and made with a binary mixture of particles of silver and carbon may be understood as a synonym to an ink conductive to electricity through particles of silver and/or carbon.

In all methods of the present disclosure a first electrical circuit containing the working electrode is thus printed on the substrate. A second electrical circuit containing the counter electrode and a third containing the reference electrode may be printed using the same printing techniques with conductive inks. However, the silver particles pollution is much less critical for the reference electrode, which is usually silver, and the counter electrode. Techniques known from the prior art without the silver depleted recess may be used for the counter electrode and reference electrode.

The three electrical circuits above together form a printed electrochemical cell if they are printed on a single substrate. The printing techniques being easily suitable for duplication by printing several printed electrochemical cells in parallel, several cells, such as described above, could be printed, according to the present disclosure, on the substrate, in parallel, in order to obtain a matrix of printed electrochemical cells. This substrate could then be bonded to a plate pierced with open wells, which are holes spanning said plate, so that each printed electrochemical cell constitutes a bottom for each open well and closes each well on one face. The wells could then be arranged with their opening remaining higher than the bottom and filled with an electrolyte and used as a complete electrochemical cell in combination with a mean of electrical multiplexing to make it possible to operate one cell after another.

Embodiments of the present disclosure are thus likely to have an industrial application in the electrochemical field.

The invention claimed is:

1. A device comprising:
   a substrate;
   an electrode;
   a track; and
   a recess, wherein the substrate extends over a first thickness, between a first face and a second face, wherein the electrode is printed on the first face, wherein the track is printed on the second face,
   wherein the substrate is electrically insulated,
   wherein the electrode is conductive to electricity essentially through carbon particles,
   wherein the track is conductive to electricity and contains particles of silver,
   wherein the recess is conductive to electricity and is made of an ink which comprises a binary mixture of carbon and silver in proportions where the quantity of silver divided by the sum of the quantities of carbon and silver present in the binary mixture is comprised within a 0 to 1 interval,
   wherein the recess extends within the substrate from the first face to the second face,
   wherein the recess is in electrical contact with the electrode at the level of a first junction located on the first face,
   wherein the recess is in electrical contact with the track at the level of a second junction located on the second face, and
   wherein the linear density of silver particles in the recess at the level of the first junction, perpendicularly to lines of a current passing through the first junction, is lower than the linear density of silver particles in the track at the level of the second junction, perpendicularly to lines of a current passing through the second junction.

2. The device according to claim 1, wherein the recess is conductive to electricity essentially through carbon particles.

3. The device according to claim 1, wherein the recess has a concentration of silver particles essentially equal to the concentration of silver particles of the track and wherein the section of the recess, parallel to the first face, at the level of the first junction, has an area lower than that of the section of the recess, parallel to the second face, at the level of the second junction.

4. The device according to claim 2, wherein the recess extends, within the substrate, according to a rotation cylinder around a cylindrical axis perpendicular to the first face.

5. The device according to claim 2, wherein the recess extends, within the substrate, according to a truncated cone around an axis perpendicular to the first face, the section of the truncated cone, parallel to the first face, decreasing from the second face to the first face.

6. The device according to claim 2, wherein the recess extends, within the substrate, according to a truncated cone around an axis perpendicular to the first face, the section of the truncated cone, parallel to the first face, decreasing from the first face to the second face.

7. The device according to claim 3, wherein the recess extends, within the substrate, according to a truncated cone around an axis perpendicular to the first face, the section of the truncated cone, parallel to the first face, at the level of the first junction, having a surface lower than the surface of the second junction.

8. The device according to claim 1, wherein the recess includes a part printed on said second face, up to the second junction.

9. A method of manufacturing a device according to claim 1, comprising:
   drilling a hole through said substrate from said first face to said second face;
   filling the hole with said ink to form said recess;
   printing, on the first face, said electrode, in electrical contact with the recess; and
   printing, on the second surface, said track, in electrical contact with the recess.

10. The device of claim 1, wherein the device is used as a working electrode of an electrochemical cell.

* * * * *